(12) United States Patent
Elsner et al.

(10) Patent No.: US 7,549,967 B2
(45) Date of Patent: Jun. 23, 2009

(54) FIXING MEANS FOR TEMPORARILY FIXING HUMAN OR ANIMAL BODY PARTS

(75) Inventors: Peter Elsner, Holzmaden (DE); Adam Geissler, Karlsdorf-Neuthard (DE); Martin Knörlein, Freiburg (DE)

(73) Assignee: Fraunhofer-Gesellschaft zur Forschung der angewandten Forschung e.V., München (DE)

( * ) Notice: Subject to any disclaimer, the term of this patent is extended or adjusted under 35 U.S.C. 154(b) by 482 days.

(21) Appl. No.: 10/591,274

(22) PCT Filed: Feb. 17, 2005

(86) PCT No.: PCT/EP2005/001617

§ 371 (c)(1),
(2), (4) Date: Aug. 31, 2006

(87) PCT Pub. No.: WO2005/087160

PCT Pub. Date: Sep. 22, 2005

(65) Prior Publication Data

US 2007/0142758 A1    Jun. 21, 2007

(30) Foreign Application Priority Data

Mar. 11, 2004 (DE) .................... 10 2004 011 872

(51) Int. Cl.
   *A61F 5/00* (2006.01)
(52) U.S. Cl. ................... 602/5; 602/8; 602/75
(58) Field of Classification Search ........ 602/5, 602/7, 8, 20–23, 26–27, 75
See application file for complete search history.

(56) References Cited

U.S. PATENT DOCUMENTS

| | | | |
|---|---|---|---|
| 6,544,204 B1 | 4/2003 | Brandhoff | |
| 6,641,900 B2 * | 11/2003 | Hebrink et al. | ............. 428/212 |
| 2001/0018567 A1 | 8/2001 | Bodenschatz | |
| 2002/0123709 A1 | 9/2002 | Goble | |

FOREIGN PATENT DOCUMENTS

| | | |
|---|---|---|
| CA | 2 326 567 | 10/1999 |
| EP | 0 305 175 | 3/1989 |
| EP | 0 352 095 | 1/1993 |
| WO | WO 02/13735 | 2/2002 |

* cited by examiner

*Primary Examiner*—Michael A. Brown
(74) *Attorney, Agent, or Firm*—Paul Vincent

(57) ABSTRACT

The invention relates to a fixing means which is used to temporarily fix human or animal body parts. The fixing means comprises at least one flexible carrier layer which is coated with a hardenable material, wherein the body part which is to be fixed can be surrounded either fully or partially by the fixing means and the hardenable material can then be hardened, wherein the carrier layer is stiffened. In order to provide for individual fixing of the body part while guaranteeing a partial adjustment of the desired rigidity of the fixing means, the fixing means is provided with at least two carrier layers, with at least one outer layer made of a flexible polymer film and at least one inner layer made of a flexible film in addition to at least one substantially liquid or viscous layer which is arranged between the outer and inner layer and which is made of at least one hardenable adhesive. It is thus possible to obtain the desired degree of rigidity when the adhesive has hardened by exerting manual pressure on the fixing agent which enables the hardenable adhesive to be displaced.

18 Claims, 1 Drawing Sheet

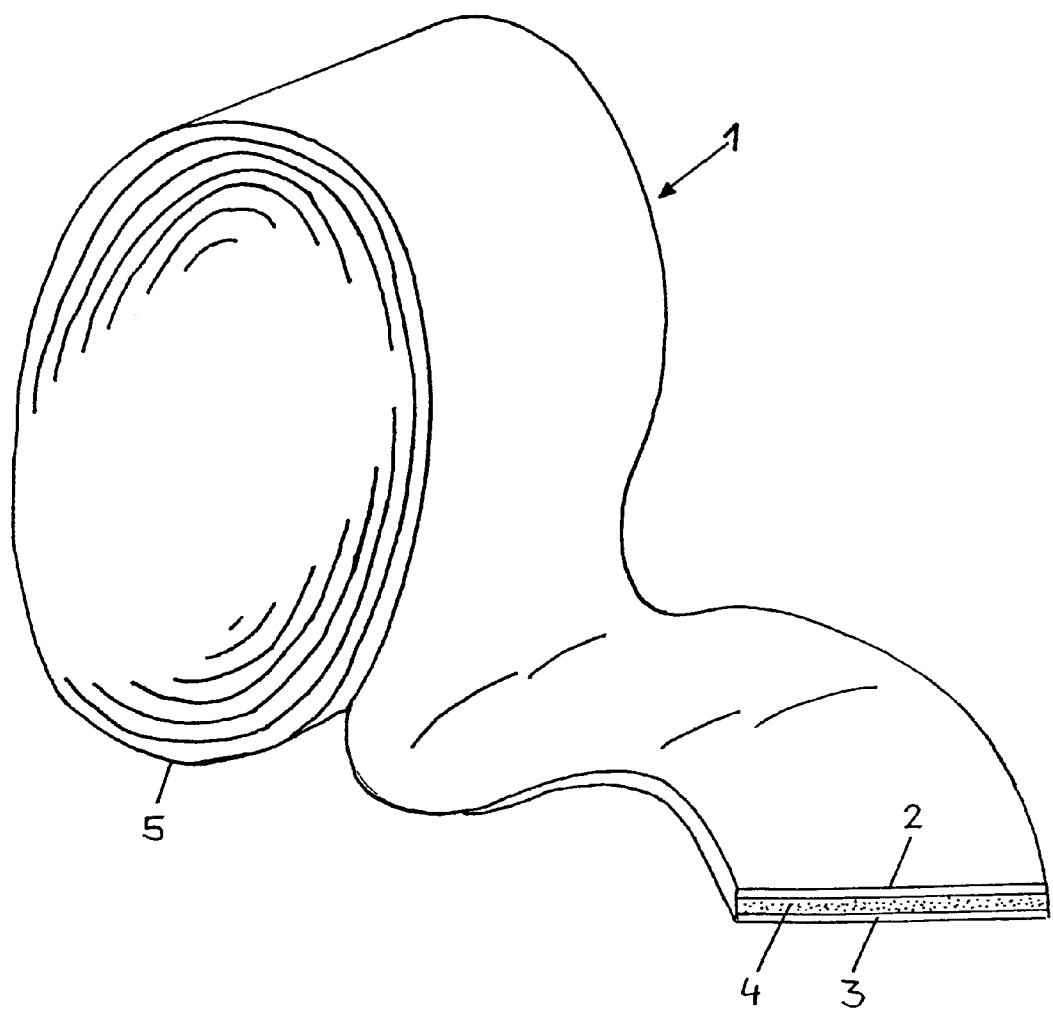

FIXING MEANS FOR TEMPORARILY FIXING HUMAN OR ANIMAL BODY PARTS

This application is the national stage of PCT/EP2005/001617 filed on Feb. 17, 2005 and also claims Paris Convention priority of DE 10 2004 011 872.8 filed Mar. 11, 2004.

BACKGROUND OF THE INVENTION

The invention concerns a fixing means for temporarily fixing human or animal body parts, comprising at least one flexible carrier layer which is coated with at least one hardenable material, wherein the body part to be fixed may be completely or partially surrounded by the fixing means and the hardenable material may then harden, thereby stiffening the carrier layer.

Temporary fixing of body parts is often required for therapeutical reasons in the field of human and veterinary medicine. This applies e.g. for bone, cartilage, joint, capsule, and tendon injuries etc. and also for post-treatment after operations, inflammations such as periostitis and tendovaginitis etc. and for numerous other injuries or diseases.

Plaster compresses made from a textile carrier material, which is coated with plaster particles, are conventionally used as fixing means. The compresses are wet and wound around the entire body part or parts thereof to be fixed, and hardened by setting of the plaster into a rigid plaster cast. Alternatively, the plaster is separately mixed with water, the textile carrier material is soaked in the dispersion and the bandage is placed around the body part and hardened.

In addition to the relatively large weight of such plaster casts, the plaster material is disadvantageously completely rigid after setting, which can have serious consequences for the patient, in particular, when the body part must be fixed for a relatively long time for medical reasons. In particular, long fixation of body parts often causes muscular atrophy, tendon hardenings, rigid joints and the like, such that the patient often suffers after removing the plaster cast, frequently requiring physiotherapeutical help.

The same applies for plastic compresses which have been recently used, which are lighter than plaster but are also completely rigid.

There are also elastic support bandages which are used alone or in connection with a fixing means such as e.g. a splint. The fixing effect of such support bandages is often insufficient for many medical indications, at least in the acute state.

DE 198 41 562 C2 describes a fixing means for temporarily fixing human or animal body parts, in the form of a synthetic strip bandage comprising a textile soaked in artificial resin, a cushion disposed below it, a sheet disposed on top of it, and a spacer which is introduced between the textile and the sheet. The extremely complex handling of the conventional fixing means is disadvantageous, since the textile soaked with artificial resin must be stored in a liquid-tight package to prevent premature hardening of the artificial resin which would render the bandage unusable. After removal of the soaked textile, the additional layers must be connected thereto, and the bandage joined in this fashion, must be applied to the patient, with the cushion in between. Special care must thereby be taken that the artificial resin does not touch and harden on the skin of the patient, which is often injured.

EP 0 352 095 B1 also discloses an orthopaedic fixing means which comprises a flexible substrate, in particular, from woven or non-woven material, which is impregnated on both surfaces with a hardenable liquid compound. Both surfaces of the impregnated substrate are covered by a material which is impermeable to the liquid compound but permeable to water. The hardenable liquid compound is hardened only by water. For this reason hardening only in certain areas or variation of the rigidity of the hardened fixing means in certain areas, which may be desired for medical reasons and/or to increase the comfort of the patient, is not possible or only to a limited degree.

WO 02/13735 A2 describes a hardenable, adhesive splint which comprises a hardenable resin, wherein hardenable resins may be provided which can be hardened i.a. using heat, electromagnetic radiation, UV and IR radiation. The splint which is formed from several components is assembled by the user and directly glued onto the skin of the patient.

DE 199 62 747 A1 discloses a further fixing means in the form of an orthopaedic bandage which has a flexible carrier material, in particular, in textile form, and a thermoplastic adhesive mass. Prior to use, the latter is transformed into a plastic state through heating, and solidified in correspondence with the contour of the body part to be fixed. This also requires more or less time-consuming pretreatment due to preheating, and precise hardening in certain areas is practically impossible.

It is the underlying purpose of the invention to further develop a simple and inexpensive fixing means for temporarily fixing human or animal body parts, thereby avoiding the above-mentioned disadvantages in such a manner that its rigidity can be varied in areas in accordance with the individual requirements.

SUMMARY OF THE INVENTION

This object is achieved in accordance with the invention with a fixing means of the above-mentioned type in that the fixing means has at least two carrier layers consisting of at least one outer layer of a flexible polymer sheet, at least one inner layer of a flexible polymer sheet and at least one substantially liquid or viscous layer of at least one hardenable adhesive which is disposed between the outer and inner layers.

The inventive fixing means permits simple individual adjustment of the rigidity in certain areas as desired or required for medical or therapeutical reasons in that, after applying the fixing means either completely or partially around the body part to be fixed, the substantially liquid or viscous adhesive is displaced or accumulated in certain areas by applying pressure onto the fixing means. This may be effected manually, e.g. through compressing the two polymer sheets or applying pressure onto the outer polymer sheet, bending the fixing means etc. or by using any auxiliary means such as rollers or the like. The adhesive layer introduced between the outer and inner flexible polymer sheet may then harden, wherein, in those areas where the adhesive layer has been completely or partially displaced, the fixing means has a relatively large resilience compared to the other, in particular completely rigid, areas. When the adhesive material has been substantially completely displaced, a maximum resilience is obtained which corresponds substantially to the resilience of the flexible polymer sheet layers. In contrast thereto and as mentioned above, the other areas of the fixing means may be completely rigid due to complete hardening of the adhesive layer at these locations. The inventive fixing means is thereby ready to use and need not be assembled from several separate components and the adhesive layer disposed between the sheet layers is reliably prevented from contacting the skin of the patient.

Clearly, the areas of different rigidity may alternatively or additionally be formed through complete hardening of certain areas of the adhesive layer and only partial or no hardening in other areas, as is explained in more detail below.

The fixing effect of the inventive fixing means which is i.a. much lighter than plaster, can therefore be exactly adjusted to the individual requirements and helps to prevent or at least reduce the problems of the patient due to long fixation of a body part, such as muscular atrophy, tendon hardenings, stiffening of joints etc. For indications, which require fixing of at least both neighboring joints, e.g. of a finger, hand, lower arm etc., e.g. the finger joints, wrist, elbow etc., the inventive fixing means also supports further neighboring joints, e.g. the wrist, elbow, shoulder etc. without having to completely fix them.

Moreover, the carrier layers of the inventive fixing means, which are designed as polymer sheet layers (described in more detail below), as well as the adhesive introduced between these layers may be transparent, such that the healing process of an injured or diseased body part is visible through the fixing means, which need not be removed and replaced by a new fixing means in order to observe the healing process.

While it is sufficient for most applications of the inventive fixing means to have only one inner and one outer layer of a resilient polymer sheet with an interposed adhesive layer, it is clearly possible to provide more polymer sheet layers, wherein the layer of a hardenable adhesive is introduced between at least two, several or even all polymer sheets of such a sandwich-type structure.

In a preferred embodiment, the adhesive is an adhesive which hardens using electromagnetic radiation, wherein at least the outer layer consists of a polymer sheet which is permeable to electromagnetic radiation. The adhesive is thereby hardened e.g. using an electromagnetic radiation source, wherein precise irradiation of those areas of the fixing means which shall be completely hardened is possible, while other areas which should only be partially hardened or not at all can be irradiated for a shorter time period, with a lower intensity of electromagnetic radiation, or not at all.

The adhesive may e.g. be an adhesive that hardens using infrared radiation, wherein infrared radiation means electromagnetic radiation of a wavelength of approximately 800 nm to approximately 1000 µm, i.e. longer than visible light.

The adhesive may alternatively be e.g. an adhesive that hardens using ultraviolet radiation, wherein ultraviolet radiation means electromagnetic radiation of a wavelength of approximately 10 nm to 400 nm, i.e. shorter than visible light but above X-ray radiation. In order to ensure maximum protection of the patient, an adhesive is preferably provided which hardens using long-wave and therefore relatively low-energy ultraviolet radiation, preferably in a wavelength range of UV-A radiation (approximately 320 nm to approximately 400 nm) through UV-B radiation (approximately 280 nm to approximately 320 nm) to UV-C radiation (approximately 200 nm to approximately 280 nm), in particular in the UV-A to UV-B region, and preferentially in the UV-A region.

In another preferred embodiment, the adhesive is an adhesive that hardens using ultrasound, wherein the fixing means may thereby be hardened only in certain areas by exposing areas of the fixing means to ultrasonic waves for different time periods and/or with different intensities using an ultrasound emitter, such as a sonotrode.

Finally, in a further preferred embodiment, the adhesive is an adhesive that hardens through heat. The adhesive may harden through body heat when complete hardening is desired, and varying rigidity is realized by localized displacement of the adhesive layer, as described above. On the other hand, the adhesive may also be selected such that hardening requires a temperature which is higher than the body temperature, e.g. in a range between approximately 40 and 60° C., in particular, between approximately 40° C. and approximately 50° C., such that the rigidity of the fixing means may vary also in this case through localized heating and thereby hardening the adhesive, without the danger of further hardening due to body heat.

The adhesive may preferably be formed from at least one hardenable resin, optionally in connection with a hardener which can be activated using electromagnetic radiation, ultrasound and/or heat. In particular, thermoplastic materials may be used as such resin systems, preferably selected from the group of acrylic resins, methacrylic resins, epoxy resins, polyester resins, polyurethane resins, urea resins, melanine resins, formaldehyde resins, phenolic resins, furane resins, silicone resins, mixtures thereof or a thermosetting material obtained through copolymerisation of several of the above-mentioned resins.

The outer and/or inner layer of the inventive fixing means is/are preferably formed from a sheet of at least one thermoplastic and/or thermoelastic polymer or a polymer blend of such polymers. Such thermoplastic sheets have sufficient flexibility to be easily manually applied to the body part to be fixed like a bandage or a compress. They can also be produced in a simple and inexpensive fashion using any conventional thermoplastic production methods, e.g. through blow molding, extrusion or the like. The inventive fixing means can be produced in a very simple and inexpensive manner e.g. by guiding the two sheet layers of a thermoplastic or thermoelastic polymer between two cylinder rollers, introducing the adhesive between the two layers and uniformly distributing it using the rollers.

In a preferred embodiment, the outer and/or inner layer is/are formed from a sheet of at least one thermoplastic and/or thermoelastic polymer with functional groups, such as polyamides, polyesters, polyurethanes, polycarbonates or the like. The functional groups of the polymer/s of the sheet layers provide excellent and permanent connection to a thermosetting resin layer which is introduced between the outer and inner layer, wherein the functional groups of the polymers of the outer and inner layers may optionally be cross-linked therewith to harden the thermosetting adhesive layer.

The layer thickness of the layers of the flexible polymer sheets or the adhesive sheet depends mainly on the body parts to be fixed, wherein in most cases, a layer thickness of between approximately 0.01 mm and approximately 5 mm, in particular between approximately 0.1 mm and approximately 2 mm, e.g. to approximately 0.2 mm is favorable for the outer and inner layer. The adhesive layer has a corresponding layer thickness of between approximately 0.01 mm and approximately 20 mm, in particular between approximately 0.1 mm and approximately 10 mm.

In a further development, at least the adhesive layer has reinforcing fibers, in particular optical fibers, to ensure particularly great solidity or rigidity of the fixing means after complete hardening of the adhesive.

In an advantageous embodiment, the layers of flexible polymer sheet and the adhesive layer are transparent, such that the fixed body part remains visible under the fixing means. This design is particularly advantageous for injuries in order to visually observe the healing process and e.g. detect an inflammation quickly without having to remove the fixing means.

The inventive fixing means may basically have any substantially planar shape. It may e.g. be rectangular, if only areas of the body part to be fixed are surrounded and the fixing means is hardened thereby forming a splint which is open on one side. The inventive fixing means may advantageously be tubular like a sleeve which can e.g. be pushed over a patient's body part to be fixed, be manually pressed into the part, followed by hardening of the adhesive layer introduced between the inner and outer layer, which are disposed in a tubular and coaxial manner, respectively.

In order to facilitate handling, it is often favorable for the fixing means to be substantially band-shaped, such that the practitioner in attendance, i.e. a doctor or veterinarian, can place the fixing means onto the body part to be fixed like a bandage and let it harden in certain or all areas.

In the latter case, the band-shaped fixing means may, in particular, be wound substantially in the form of a roll.

The invention is described in more detail below by means of an embodiment and with reference to the drawing.

BRIEF DESCRIPTION OF THE DRAWING

The single FIGURE shows an embodiment of a fixing means for temporarily fixing human or animal body parts, in the form of a band-shaped bandage material.

DESCRIPTION OF THE PREFERRED EMBODIMENT

The fixing means 1 shown in the drawing is designed like a bandage and wound substantially into a roll. The band-shaped fixing means 1 comprises an outer layer 2 and an inner layer 3 which are each formed from a resilient plastic sheet of a thermoplastic polymer, e.g. polyamide. The layer thickness of the outer 2 and inner layer 3 is e.g. 0.06 mm. A layer 4 of a hardenable adhesive in the form of a viscous, thermosetting resin mixture is introduced between the outer 2 and inner layer 3, having a layer thickness of e.g. approximately 5 mm.

The resin mixture may e.g. consist of 70 mass % of isobutyl methacrylate, 20 mass % of 1.3 butane diol dimethacrylate and approximately 10 mass % of trimethylol propane trimethacrylate and be mixed with approximately 1 to 3 mass % (related to the resin mixture) of a photochemical hardening agent in the form of diphenyl(2,4,6 trimethyl benzoyl)=phosphine oxide (trade name: Lucirin TPO® of BASF AG).

In the present embodiment, the band-shaped fixing means 1 is wound to form a roll 5 which has approximately the shape of a gauze bandage and can be easily wound about the body part to be fixed. The layers 2, 3 and the adhesive layer 4 are substantially transparent, wherein the adhesive layer 4 may optionally contain microfibers, e.g. glass fibers, for reinforcement.

We claim:

1. A fixing means for temporarily fixing human or animal body parts, with at least one flexible carrier layer which is coated with at least one hardenable material, wherein the body part to be fixed is surrounded either completely or partially by the fixing means, and the hardenable material is then hardened, thereby stiffening the carrier layer, the fixing means comprising:
at least one outer layer of a flexible polymer sheet;
at least one inner layer of a flexible polymer sheet; and
at least one substantially liquid or viscous layer of at least one hardenable adhesive disposed between said outer and said inner layers, wherein said outer and inner layers of said flexible polymer sheets as well as said adhesive layer are transparent such that a fixed body part remains visible beneath the fixing means.

2. The fixing means of claim 1, wherein said adhesive can be hardened using electromagnetic radiation, wherein at least said outer layer consists of a polymer sheet which is permeable to electromagnetic radiation.

3. The fixing means of claim 2, wherein said adhesive is an adhesive that can be hardened using infrared radiation.

4. The fixing means of claim 2, wherein said adhesive is an adhesive that can be hardened using ultraviolet radiation.

5. The fixing means of claim 2, wherein said adhesive is an adhesive that can be hardened using ultrasound.

6. The fixing means of claim 2, wherein said adhesive is an adhesive that can be hardened using heat.

7. The fixing means of claim 1, wherein said adhesive is formed from at least one hardenable resin.

8. The fixing means of claim 7, wherein said resin comprises a hardener which can be activated by electromagnetic radiation, ultrasound, and/or heat.

9. The fixing means of claim 7, wherein said adhesive comprises a thermosetting material.

10. The fixing means of claim 9, wherein said thermosetting material is selected from the group consisting of acrylic resins, methacrylic resins, epoxy resins, polyester resins, polyurethane resins, urea resins, melanine resins, formaldehyde resins, phenolic resins, furane resins, silicone resins, and mixtures thereof.

11. A fixing means comprising a thermosetting material obtained through copolymerisation of one or several of the resins of claim 10.

12. The fixing means of claim 1, wherein said outer and/or said inner layer are formed by a sheet of at least one thermoplastic and/or thermoelastic polymer.

13. The fixing means of claim 12, wherein said outer and/or said inner layer are formed by a sheet of at least one thermoplastic and/or thermoelastic polymer having functional groups, polyamides, polyesters, polyurethanes, or polycarbonates.

14. The fixing means of claim 1, wherein said outer and said inner layers have a layer thickness of between 0.01 mm and 5 mm or between 0.1 mm and 2 mm.

15. The fixing means of claim 1, wherein said adhesive layer has a layer thickness of between 0.01 mm and 20 mm or between 0.1 mm and 10 mm.

16. The fixing means of claim 1, wherein said adhesive layer has reinforcing fibers or glass fibers.

17. The fixing means of claim 1, wherein the fixing means is substantially band-shaped.

18. The fixing means of claim 17, wherein the fixing means is substantially wound into a roll.

* * * * *